United States Patent [19] [11] 4,296,752
Welsh et al. [45] Oct. 27, 1981

[54] TRANSCUTANEOUS OXYGEN SENSOR WITH ADJACENT HEATER

[75] Inventors: Luther Welsh, San Clemente; Daryl J. Bergquist, Huntington Beach; Hideo Watanabe, Fullerton, all of Calif.

[73] Assignee: Johnson & Johnson, New Brunswick, N.J.

[21] Appl. No.: 37,650

[22] Filed: May 11, 1979

Related U.S. Application Data

[62] Division of Ser. No. 726,710, Sep. 24, 1976.

[51] Int. Cl.³ .............................................. A61B 5/00
[52] U.S. Cl. ................................ 128/635; 204/195 B
[58] Field of Search .............................. 128/635, 632; 204/195 B, 195 P

[56] References Cited

U.S. PATENT DOCUMENTS

| | | | |
|---|---|---|---|
| 3,664,178 | 5/1972 | Spergel et al. | 128/635 |
| 3,795,239 | 3/1974 | Eberhard et al. | 128/635 |
| 3,826,730 | 7/1974 | Watanabe et al. | 204/195 P |
| 3,918,434 | 11/1975 | Lübbers et al. | 128/654 |
| 3,998,212 | 12/1976 | Reichenberger | 128/635 |
| 4,005,700 | 2/1977 | Parker | 128/632 |
| 4,114,602 | 9/1978 | Huch et al. | 128/635 |
| 4,185,620 | 1/1980 | Hagihara | 128/635 |

OTHER PUBLICATIONS

Scacci, R., et al., Med. Instrumentation, vol. 10, No. 4, pp. 192-194, Jul.-Aug., 1976.

Primary Examiner—Kyle L. Howell
Attorney, Agent, or Firm—Knobbe, Martens, Olson, Hubbard & Bear

[57] ABSTRACT

A transcutaneous gas sensor for application to the skin of a patient for bloodless measurement of a partial gas pressure comprises a separable sensing cell and a circumferential heater, the heater being in direct thermal contact with the skin of the patient but not in contact with the permeable sensing face of the sensor cell. A differential temperature measuring thermocouple is utilized to monitor the temperature of the patient's skin and the temperature of the heater to provide a warning of a decrease in local perfusion in the area of the sensing cell.

10 Claims, 9 Drawing Figures

FIG. 1.
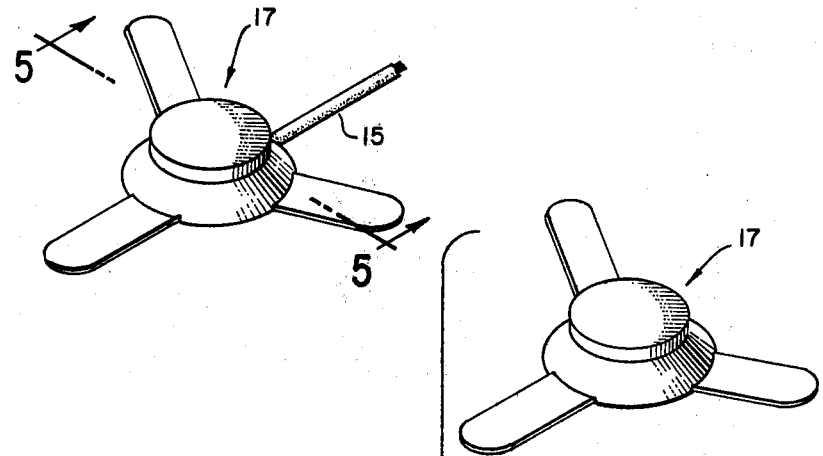
FIG. 2.
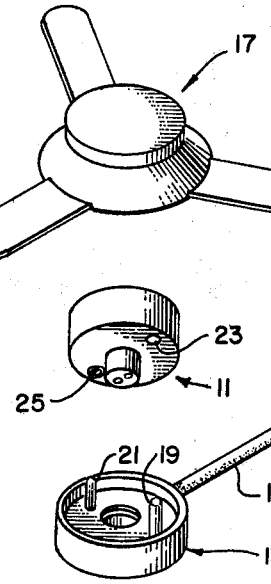
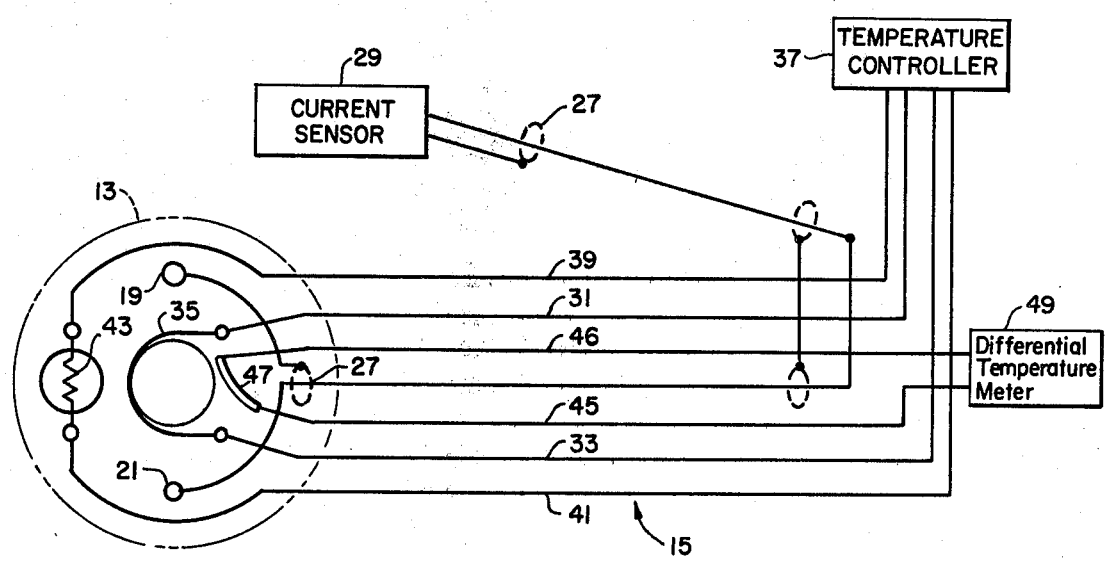
FIG. 3.

TRANSCUTANEOUS OXYGEN SENSOR WITH ADJACENT HEATER

This is a division of application Ser. No. 726,710, filed Sept. 24, 1976.

BACKGROUND OF THE INVENTION

This invention relates to sensors for use in the surface measurement of a partial pressure of a gas in the blood of a patient by use of polargraphic cells or sensors. In the prior art such sensors have been known for several years and it has been determined that in vivo or surface measurements utilizing these devices produce results which are a function both of the partial pressure of the gas in the blood and of the local blood circulation in the region immediately adjacent to the area where the measurement is taken. Since this area is generally very small, typically 0.5 square centimeters or less, it has been found practical to hyperaemise the skin and the subjacent tissue as a method of reducing the dependence of the sensor on the local blood circulation and to thereby produce a more accurate reading of the true partial pressure of the measured gas in the blood. While this may be accomplished by chemical methods, using vasodilating compounds such as histamine, nicotinic acid, etc., the same result has been more conveniently accomplished by the application of heat to the skin, which also produces local hyperaemisation.

Prior devices which use heat to hyperaemise the skin suffer from several shortcomings to which the invention herein is directed. Initially, heat is applied from within the sensing cell in such devices and passes heat directly through the sensing face of the sensing cell to the skin. This is the method, for example, of Eberhard et al, U.S. Pat. No. 3,795,239. This direct heating of the sensor membrane and electrolyte adjacent to the membrane decreases the useful life of the sensor and results in increased cost to the user both directly by making necessary the purchase of extra sensor units and indirectly by consuming personnel time to replace the in vivo sensor. A principle result of the current invention is improved economy through the superior heater arrangement resulting in longer equipment lifetime without a significant reduction of the hyperaemisation in a region subjacent to the sensor.

A second problem in the current art has been an observed downward drift in readings by the instruments attached to the transcutaneous sensor in the absence of any real reduction in arterial blood gas level as measured directly. The origin of this long term drift is not precisely known, although the configuration of the instant invention has been observed to have significantly less drift. It is hypothesized that the drift is due to local edema in the immediate vicinity of the sensor membrane caused by the application of heat over prolonged periods of time and the associated hyperaemisation immediately below the sensor membrane. The instant invention has a remarkedly reduced instrument drift thought to be the result of the avoidance of directly heating the skin beneath the sensor membrane and thus not subjecting that skin area to welting or other effects which commonly occur after the prolonged application of heat to the skin surface.

An additional result of the present invention is the obtaining of accurate readings at slightly lower average temperatures than is currently practiced. The present invention will have as its principle application the measuring of transcutaneous oxygen levels in prematurely born children. The constant application of heat to their skin creates a blistering problem. Current devices operate at a heater temperature of 45° C. and a skin temperature of 43° C., whereas the present invention works reliably at a temperature of about 43° C. and a skin temperature of 41° C. This small reduction in temperature helps to guard against blistering.

The present invention also provides an improved and economical method of measuring the blood perfusion in the area of the sensor membrane by use of a differential temperature measurement. Previously a local circulatory failure in the region of the sensor was only determined by measuring the energy consumption necessary to maintain the heater at a constant temperature. In the event of a circulatory failure, either locally at the membrane measurement site or a general failure, the cooling effect of blood flowing through the subjacent skin would decrease, resulting in decreased energy consumption of the heater. This energy consumption would be monitored as a means of detecting the circulation failure, but has certain drawbacks. It is not responsive directly to the blood circulation and perfusion near the membrane, but rather is a measure of all of the cooling elements around the heater, only one of which is the skin. Thus, this method is responsive to the thermal capacity of the heater and total environment surrounding the heater, only one portion of which is the cooling effect of the blood perfusion under the skin. Finally, it should be noted that the present invention is especially adaptable for use with disposable cartridge sensors of the type described in U.S. Pat. No. 3,826,730 of Watanabe and Leonard. However, the principles of this invention could be practiced with other sensor cells with minor structural modifications.

In the prior art it has been common to utilize electric heating wire for heating sensors to raise the skin temperature. Such heating coils generally create temperature differentials within the sensor itself, often generating hot spots on the sensor surface which damage or blister the patient's skin. This is caused to a great extent by the inability of the small sensor body to properly distribute the heat generated by the heating coil throughout the sensor structure.

SUMMARY OF THE INVENTION

A sensing cell for the in vivo detection of a partial pressure of a gas in the blood by transcutaneous measurement is provided with a circumferential heater which is not in contact with the permeable membrane of the cell at its sensing face or in contact with the electrolyte immediately behind the membrane. This results in a longer cell life and reduced instrument drift over long term operation. Additionally, there is included a differential temperature sensing apparatus for detecting the temperature difference between the heater itself and subjacent skin. This provides an accurate and rapid means for detecting any changes in the blood perfusion in the area of the sensing membrane, enabling the rapid detection of any errors caused by such changes.

Furthermore, the present invention incorporates a heating system in one embodiment which raises the temperature of the skin surrounding the sensor through the use of a heat transfer fluid, this fluid being closely controlled in temperature and less likely to generate hot spots on the surface of the sensor and the skin. The heating of adjacent skin areas makes the present sensor particularly adaptable to use with a disposable sensor cartridge which may be placed centrally within the circumferential heater and may be replaced without replacing the heater assembly.

These and other advantages of the present invention are best understood through a reference to the drawings, in which:

FIG. 1 is a perspective view of the assembled sensor of the present invention;

FIG. 2 is an exploded view showing the basic components of the sensor of FIG. 1;

FIG. 3 is an electrical schematic diagram showing the main electrical elements of the sensor of FIG. 1 and the interconnection of those elements to the monitoring equipment used in conjunction therewith;

DETAILED DESCRIPTION OF THE PREFERRED EMBODIMENT

Figure 4:
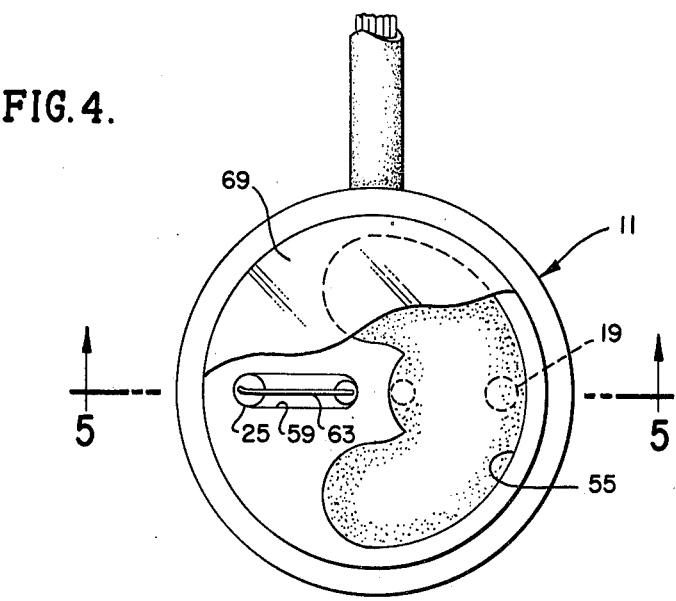
FIG. 4 is a plan view, partially in section along lines 4—4 of FIG. 5, of the sensor of this invention.

Referring initially to FIGS. 1 and 2, a transcutaneous gas partial pressure sensor of the present invention is shown as including two primary elements: a disposable sensing element 11 and a permanent interconnection and heating element 13 interconnected by a multiple conductor cable 15 to sensing instrumentation. The sensor 11 and interconnect and heater 13 are designed to fit together into a plastic butterfly cap 17 which serves to hold the sensor 11 and interconnect 13 together and to form a foundation for taping the members onto the skin of an infant or other patient. It will be understood that the butterfly cap 17 is a standard item and is used only as a mechanical mounting apparatus to hold the sensor 11 and interconnect 13 tightly against the skin of the patient. It will also be recognized that a small amount of water or lubricant may be placed between the skin of the patient and the sensing cell 11 to prevent gas leakage into the sensing cell 11 from the outside atmosphere.

As specifically shown in FIG. 2, an anode 19 and a cathode interconnect 21 project from a face of the interconnect assembly 13. The anode 19 is received in an anode aperture 23 on one face of the sensor 11 and the cathode interconnect 21 is received in a cathode connection receptacle 25 in the sensor 11. The elements 19 through 25, in addition to making the necessary electrical connections between the multiple conductor cable 15 and sensor 11, serve to mechanically mount the sensor 11 on the interconnect assembly 13.

Referring now to FIG. 3, the interconnect assembly 13 is shown with its electrical elements schematically diagrammed to provide an understanding of the interconnection between these elements and the sensing instrumentation used for measuring the gas partial pressure. As previously described, the interconnect assembly 13 includes an anode 19 and a cathode connector 21. These elements are connected by a shielded wire pair 27 to a current sensor 29 as is commonly used with prior art sensors. This current sensor 29 presents a voltage potential between the anode 19 and cathode connector 21 and monitors the current flow between these elements in response to this regulated potential. As will be described in detail below, the current flow provides an indication of the partial pressure of the monitored gas within the blood of the patient.

The multiple conductor cable 15 also provides a pair of wires 31 and 33 for interconnecting a heating coil 35 within the interconnect assembly 13 to a temperature controller 37. This temperature controller 37 is additionally connected by a pair of wires 39 and 41 to a thermistor 43, or other temperature sensitive element such as a thermocouple, to monitor the temperature of the interconnect assembly 13 and thereby provide a feedback for the temperature controller 37 to vary the current through the heater coil 35 and thus precisely control the temperature of the interconnect assembly 13.

The multiple conductor lead 15 also includes a pair of wires 45 and 46 connecting a thermocouple 47 to a differential temperature meter 49. The thermocouple 47 inclues a pair of thermocouple junctions, one of which is positioned to monitor the temperature of the heater and interconnect assembly 13 and the other of which is positioned to monitor the temperature of the patient's skin. Thus, the differential temperature meter 49 monitors the differential temperature between the heater and interconnect assembly 13 and skin of the patient to provide an indication of blood perfusion reduction.

It will be understood that the differential temperature meter 49 and temperature controller 37 are well known commercial devices, and their details are not described herein in the interest of brevity.

Figure 5:
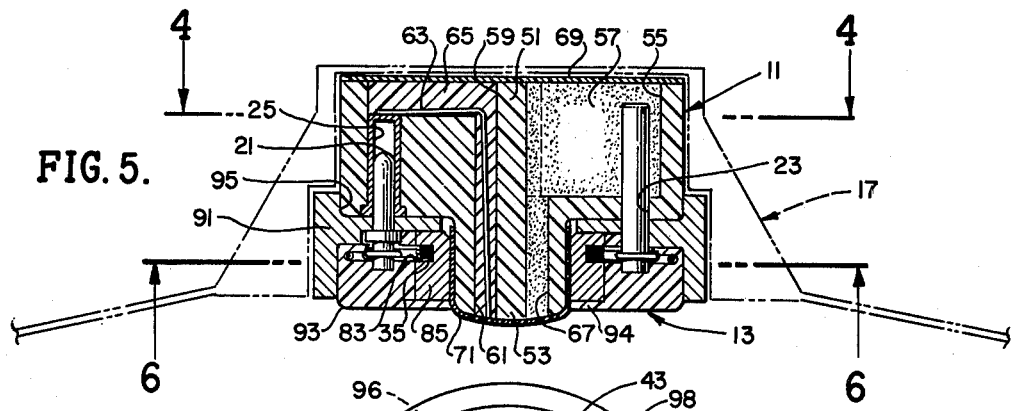
FIG. 5 is a sectional view taken along lines 5—5 of FIG. 4.

Referring now to FIGS. 4-7, the detailed structure of the sensing element 11 and interconnect and heating assembly 13 will be described. It should be noted that in each of these Figures the sensing element 11 and interconnect and heating member 13 are shown coupled to one another to form a sensing assembly, the members being held in position against one another as described previously by the positioning of the anode 19 within the anode aperture 23 and the positioning of the cathode interconnect 21 within the interconnect receptacle 25. The disposable part of the system, that is, the sensing element 11, comprises a nonconductive main body portion 51 formed, for example, of polymeric material. The body 51 is in the shape of a relatively thick circular disk with a unitarily protruding, axially centered, cylindrical extension 53, so that the body member 51 is generally T-shaped in section as shown in FIG. 5. The upper disk portion of the body 51 includes a reservoir 55 containing an electrolyte material 57 in gell form. The reservoir 55 is designed to include as much of the body member 51 as possible without interfering with proper electrical isolation of the cathode interconnect receptacle 25 and its connection to the cathode. Thus, as shown in FIG. 4, the receptacle 55 is generally arcuate in shape and extends more than half way around the circumference of the main body member 51.

The cathode interconnect receptacle 25 is formed as a deep, cup-shaped, electrically conductive member formed, for example, from metal. This receptacle 25 is permanently molded into the main body 51 at a location in the main, disk-shaped portion of the body 51 surrounding the extension 53. Alternatively, the receptacle 25 may be a force fit within a bore in the main body 51, the bore extending to communicate with a lateral slot 59 formed in the upper surface of the main body 51. This slot 59 in turn communicates with a bore 61 which passes all the way through the main body 51 to provide an opening in the exposed end of the extension 53. A cathode wire 63 is attached, as by welding, to the outer surface of the receptacle 25, passes along the slot 59 and bore 61 to extend out of the open end of the extension 53. After positioning the cathode element 63 and attaching it to the receptacle 25, the slot 59 and bore 61 may be filled with epoxy 65, and the end of the extension 53 may be ground to a smooth, domed shape as shown in FIG. 5 with the small end of the cathode element 63 presenting an extremely small exposed cathode area.

The reservoir 55 communicates by way of a bore 67 with the exposed outer face of the extension 53, and additionally communicates by way of the aperture 23 with the area below the main body 51. After insertion of the epoxy 65 and electrolyte 57 into the main body 51, the upper surface of the main body 51 may be sealed, as by a sheet of moisture and vapor impervious material 69, to prevent evaporation of the electrolyte 57. It will be understood that, during storage of the sensor portion 11, the electrolyte 57 in gell form will not appreciably escape or evaporate through the small aperture 23. However, this aperture, if desired, may be sealed prior to use of the sensor 11.

A membrane 71 selectively permeable to the gas whose partial pressure is to be analyzed is formed over the extension 53 and sealed to this extension, and particularly to the cylindrical wall thereof, to closely conform the membrane 71 to the contours of the extension 53. The electrolyte 57 will wet the exposed end of the extension 53, including the exposed end of the cathode 63, so that electrolyte communication is formed above the membrane 71 between the exposed end of the cathode wire 63 and the electrolyte within the bore 67.

Figure 6:
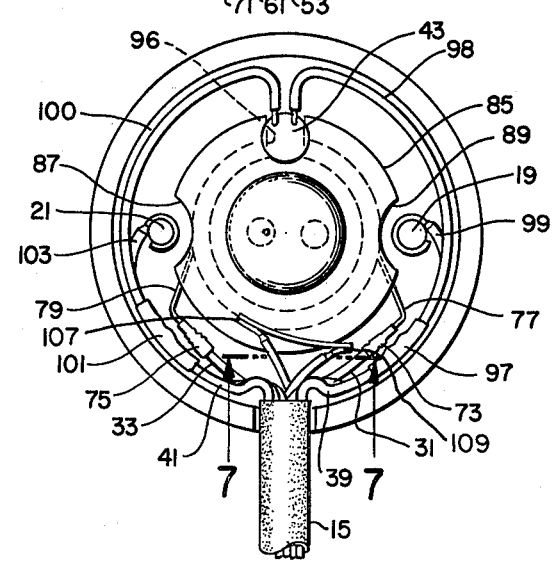
FIG. 6 is a sectional view taken along lines 6—6 of FIG. 5.
Figure 7:
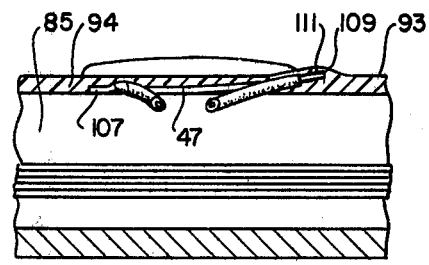
FIG. 7 is a sectional view taken along lines 7—7 of FIG. 6.

Turning now to FIGS. 5, 6, and 7, the detailed construction of the heater and interconnect assembly 13 will be described. It will be seen that the interconnect assembly 13 is connected to the pair of heater wires 31 and 33 also shown in FIG. 3 by means of electrical connectors 73 and 75, respectively, which are in turn connected to the opposite ends 77 and 79 of the electrical heater coil 35. This coil 35 is wrapped within a groove 83 formed in the outer cylindrical wall of an annular heating block 85. The heating block 85 is preferably made of a material which is not electrically conductive but is thermally conductive. Alternatively, the block 85 may be made of metal and insulated from the heater coil 35. The heater block 85 is sized to fit around the extension 53 of the sensor 11 and, in particular, around the membrane 71, but is designed to have sufficient clearance with the membrane 71 so that substantial heat is not coupled from the block 85 directly to the sensor 11. It will be seen that the heater block 85 is cut away at 87 and 89 (FIG. 6) to provide sufficient clearance for the anode 19 and cathode interconnect 21. The cathode interconnect 21, anode 19, and heater block 85 are each held in place between a pair of plastic or epoxy annular elements 91 and 93, the element 91 providing a shoulder 95 for receiving the sensor 11 while the annular element 93 provides a surface surrounding the cylindrical extension 53 when the sensor 11 and interconnect 13 are engaged. In the preferred embodiment, the member 91 is machined from polymeric material and positioned on the heater block 85. The member 93 is then formed by filling the annular cavity provided by the member 91 and heater block 85 with epoxy and curing this member 93 to a solid state. The epoxy preferably provides a thin layer 94 between the heater block 85 and the skin of the patient.

The cathode interconnect 21 may take the form of a post which is sized to frictionally engage the receptacle 25. The anode 19 is sized to be tightly receiving within the aperture 23 and is sufficiently long to penetrate the reservoir 55 so that it contacts the electrolyte 57 when the elements 13 and 11 are interconnected. Each of the anode 19 and cathode interconnect 21 may be bonded to the epoxy member 93 to provide rigid mounting of these members and to allow the interconnect member 13 to be successively applied to numerous disposable sensors 11 without damage.

The shielded wire pair 27 (FIG. 3) entering from the multiple conductor cable 15 is separated (not shown) at the junction or cable 15 and interconnect member 13 to permit separate connections to the central conductor and shield. The shield is attached to an insulated lead 99 which is wrapped around one end of the anode 19 and attached thereto, as by welding. Similarly, the central conductor of the shielded wire pair 27 is coupled to an insulated lead 103 which is wrapped around and electrically connected to the cathode interconnect 21. The thermistor 43 is inserted in a groove 96 in the heater block 85 for directly monitoring the temperature of the heater block 85, and is connected to leads 39 and 41 of the multiple conductor cable 15 by insulated leads 98 and 100, respectively, and insulated electrical interconnect members 97 and 101, respectively.

The thermocouple 47 includes a pair of thermocouple junctions 107 and 109 best shown in FIGS. 6 and 7. Junction 109 is positioned in the annular epoxy member 93 extremely close to the skin abutting surface thereof, as in the thin layer 94, so that it preferably forms a protuberance 111 on the front face of the annular member 93 to form as close a thermal contact with the skin of the patient as possible. The remaining thermocouple junction 107 is fitted flush against the heater block 85 to form a close thermal connection therewith. If desired, the junction 107 may be placed in thermistor groove 96 to assure good thermal communication with heater block 85 close to the thermistor 43. By thus utilizing the insulating properties of the annular epoxy member 93, the thermocouple junction 109 is used to monitor the temperature of the patient's skin while the thermocouple junction 107 is used to monitor the temperature of the heater block 85, and the thermocouple pair 47 is thus used to monitor the temperature differential between the heater block 85 and the patient's skin.

Referring once again to FIG. 3, it can be seen that the temperature sensor in the form of thermocouple 43 provides an output signal on lines 39 and 41 which may be processed by conventional means and displayed on a meter of the temperature controller 37. The heating coil 35 may be controlled by the temperature controller 37 using the thermistor 43 as a feedback element, so that the heater block 85 is maintained at a constant temperature. The temperature of the heater block 85 in actual use will generally be between 43° C. and 45° C. The sensor configuration of the present invention has been found to be accurate at the lower end of this range. Since the principle expected application of the present invention will be on newborn premature infants, operation at this lower end of the temperature range is valuable in minimizing the danger of blistering the skin over long periods of use.

In addition, the thermocouple 47 produces a temperature differential voltage which is monitored by conventional means on the differential temperature meter 49 and may be displayed for observation. Alternatively, it may be used to automatically operate an alarm. The use of a thermocouple in this manner, one thermocouple junction applied to the skin of a patient and the other to the heater block 85, results in a very accurate reading of the temperature difference between the skin and the heater block 85. In operation, this temperature difference will typically be 1° C. to 1.5° C. at its steady state condition. An alternative embodiment to the present form of the invention would be the use of thermistors instead of thermocouple elements, a pair of thermistors being applied to the heating block 85 and the skin of the patient, and a standard differential temperature monitoring device used to generate a temperature difference measurement.

If, after reaching a stable condition in operation, there is a reduction in the blood circulation in the area of the thermocouple 47, there would be an observable reduction in the measured temperature differential as cooling by blood perfusion ceases or decreases. A technician monitoring the meter 49 which displays this temperature differential would be immediately alerted to the existence of this problem which would result in an inaccurate reading by the sensing cell. Alternatively, an alarm could be made to sound to notify the technician that blood perfusion has ceased or decreased.

The use of the heater block 85 in the area surrounding the extension 53 of the sensor 11 serves multiple purposes. Initially, it permits heating of the skin in an area surrounding the sensor 11 without directly heating the sensor 11. Thus, the long term effects of heating the skin which have been observed in transcutaneous partial gas pressure measurements, such as blistering of the skin, if they occur at all with the present invention, will occur only in the area adjacent to the sensor, and the accuracy of measurements made by the sensor 11 at the extension 53 will not be affected. Thus, the slow drift of partial pressure gas measurements during prolonged usage will not occur in the same pronounced manner in this sensor as with prior sensors where the sensing element itself was directly heated to apply heat to the skin. Secondly, the heater element in this application may be used over and over again, only the sensor 11 being replaced for repeated usage. Thirdly, the surrounding heater element 13 permits the heating of a relatively large area of skin surrounding the sensor. It will be understood that the sensor is advantageously maintained relatively small to limit the diffusion zone within the patient's skin. With the present sensor, the diffusion zone may be made very small and, in fact, may be made to approximate the surface of the sensor membrane 71, while perfusion is maintained over the larger area of the heater 13. Thus, long term inaccuracies are avoided, the initial accuracy of the device is increased by maintaining a larger heated skin area and by not directly heating the sensor 11, and it has been found that lower heater temperatures may be employed. The use of the thermocouple 47 and differential temperature meter 49 provides an accurate monitoring of blood perfusion in the sensor area and thus avoids at least part of the danger of inaccurate measurements due to poor blood perfusion.

It will be appreciated by those familiar with this art that the membrane 71 is selectively permeable by the gas whose partial pressure is being monitored. Passage of the gas through the membrane 71 permits the formation of a reduction product at the cathode 63 and a resulting current flow between the cathode 63 and anode 19, by way of the electrolyte 57. Thus, when this current is monitored, a direct reading of the partial pressure of the gas being monitored at the membrane 71 may be made. For the measurement of partial oxygen pressures, for example, the membrane 71 may be formed of teflon, the cathode 63 of gold, and the anode 19 of silver.

Figure 8:
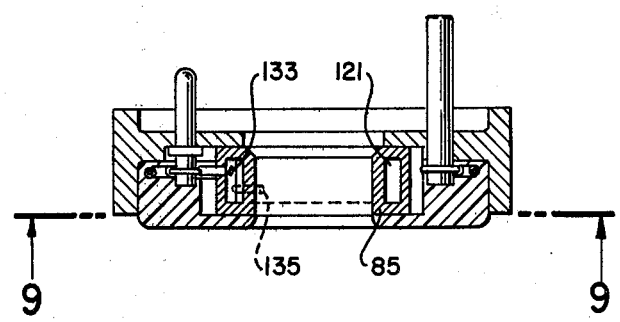
FIG. 8 is a sectional view of the heater and the mounting assembly portion of an alternate embodiment of the present invention similar to the sectional view of FIG. 5 and taken along lines 8—8 of FIG. 9.
Figure 9:
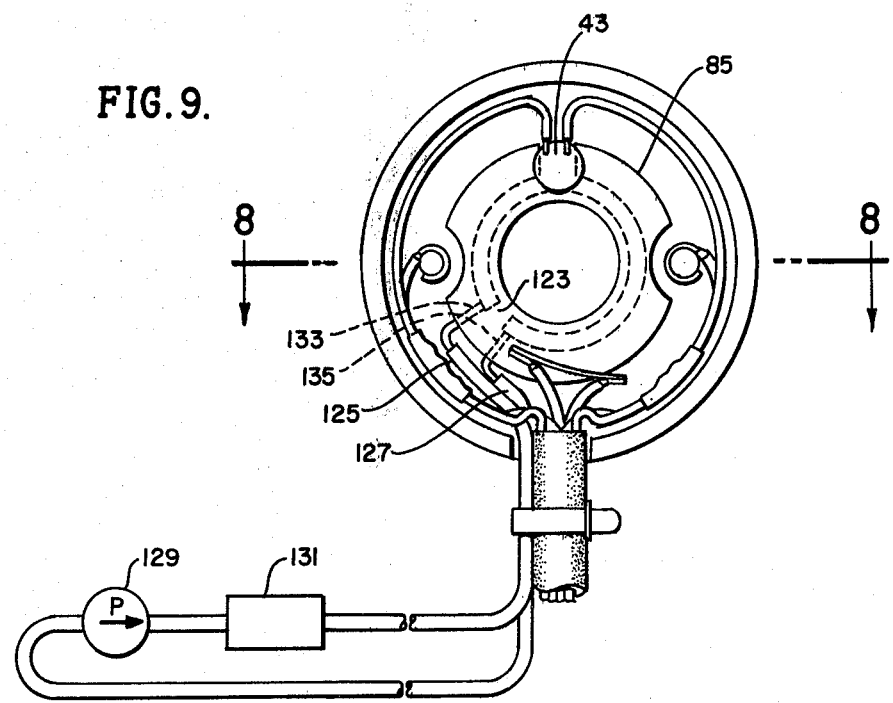
FIG. 9 is a sectional view taken along lines 9—9 of FIG. 8 showing the alternate embodiment thereof and additionally showing in schematic form the connections made for heating in the sensor.

Referring now to FIGS. 8 and 9, an alternate embodiment of the present invention will be described. This embodiment is identical in all respects to that of FIGS. 1–7, except that the heater coil 81 is replaced by an annular cavity 121 within the heater block 85. This annular cavity extends throughout all but a small portion 123 of the circumference of the heater block 85, and is used to carry a heat transfer fluid for heating the heater block 85. It has been found that the heater coil 81 can generate hot spots within the heater block 85 which can burn or blister a patient's skin, even though the heater block 85 is at the correct operating temperature. The heat transfer fluid used in the device shown in FIGS. 8 and 9 does not generate hot spots, since a large interior surface of the heater block 85 is contacted by the fluid. The embodiment of FIGS. 8 and 9 therefore replaces the heater 85 and its associated wires 31 and 33 with the annular cavity 121 and interconnecting tubular conduits 125 and 127 which are connected at opposite ends of the annular cavity 121. A heat transfer fluid may be pumped by pump 129 through a heater 131 to continuously circulate heat transfer fluid through the heater block 85. The heater 131 may include an internal temperature sensor to maintain the temperature of the circulating fluid at the proper value, or, alternatively, may be connected to the thermistor 43 to control the heater 131 in accordance with the temperature of the heater block 85. It will be seen from FIG. 9 that the conduits 125 and 127 are connected through bores 133 and 135 to the cavity 121 for fluid circulation.

The present invention therefore comprises a means of uniformly heating the heating block 85 which is attached to the skin of the patient in an area adjacent to the sensor membrane 71, without directly heating the sensor 11 or its membrane 71.

What is claimed is:

1. A sensor for transcutaneous measurement of partial pressure of gas, comprising:
   a heater assembly;
   a transcutaneous gas sensing cell which includes (a) a cathode, (b) a reservoir, (c) a membrane, and (d) electrolyte in the reservoir and forming an electrolyte path between the cathode and the reservoir;
   said membrane including (i) a first portion having a front side disposed for direct contact with the patient's skin, and a back side adjacent the cathode but being separated from the cathode by a layer of said electrolyte defining said electrolyte path, and (ii) a second portion surrounding the gas sensing cell and disposed to be out of contact with the skin of the patient when the sensor is in use;
   said heater assembly comprising (i) an annular heat conductive element surrounding said gas sensing cell but so spaced therefrom that heat is substantially not coupled from said element directly to said gas sensing cell, and (ii) means for heating said element;

said heater assembly being so constructed, disposed and spaced relatively to said gas sensing cell as to be attachable to the skin of the patient for transfer of heat from said element to the skin, without such heat passing to the skin through the membrane and without substantial transfer of heat from said element to said gas sensing cell.

2. The sensor of claim 1 further comprising temperature differential sensing means comprising a first temperature sensitive junction so disposed and constructed as to sense the temperature of the heater block, a second temperature sensitive junction so disposed and constructed as to sense the temperature of the skin of the patient, which in use, is being heated by the heater block, and means for conducting a temperature differential signal from said junction.

3. The sensor of claim 2 further comprising temperature control means for regulating the temperature of the heater block.

4. A sensor as defined in claim 1 wherein said conducting means is an annular block positioned to circumferentially surround said sensing cell.

5. A sensor as defined in claim 1 additionally comprising:
   an anode permanently attached to said conducting means;
   a reservoir in said sensing cell for holding electrolyte, said reservoir including an aperture for receiving said anode.

6. A sensor as defined in claim 1 additionally comprising:
   a cathode mounted in said sensor cell;
   a first electrical connector mounted on said sensor cell and electrically connected to said cathode; and
   a second electrical connector mounted on said conducting means and removably connected to said first connector.

7. A sensor as defined in claim 1 wherein said heating means comprises:
   a flow conduit through said conducting means;
   a heat transfer fluid in said flow conduit, and means for heating said heat transfer fluid to a regulated temperature and for circulating said heat transfer fluid through said flow conduit.

8. A sensor for transcutaneous measurement of partial pressure of gas comprising:
   respectively detachable first and second assemblies;
   said first assembly defining an annular form penetrated by an opening, and including (a) heating means and an annular thermally conductive path means surrounding said opening, for heating a lower surface of said first assembly, said lower surface being adapted to contact the skin of the patient, and (b) respective cathode and anode connectors disposed radially outwardly of said path means, said heating means and path means defining voids for thermal insulation of said cathode and anode connectors; and
   said second assembly defining a transcutaneous gas sensing cell having a sensor portion adapted to penetrate said opening in said first assembly, said sensor portion including (a) a cathode, (b) an electrolyte reservoir, and (c) a membrane adapted to engage the skin of the patient through said opening and further to isolate physically and to insulate thermally said sensor portion from said conductive path means, said second assembly further including (d) means for engaging said cathode with said cathode connector (e) and means for coupling said anode connector with said reservoir;
   whereby said first assembly conveys heat to the skin of the patient, substantially totally through said path means and exclusively of said second assembly.

9. A sensor as defined in claim 8 wherein said first and second electrical connectors are constructed to physically interconnect said sensor cell and said conducting means.

10. A sensor as defined in claim 8 additionally comprising:
    means for making plural electrical connections between said sensor cell and said conducting means, said connecting means providing the exclusive electrical connections to said sensor cell.

* * * * *